(12) United States Patent
Crockatt et al.

(10) Patent No.: US 11,912,656 B2
(45) Date of Patent: Feb. 27, 2024

(54) OXIDATION OF 5-HYDROXY-2-FURANONE TO MALEATES

(71) Applicant: Nederlandse Organisatie voor toegepast-natuurwetenschappelijk onderzoek TNO, 's-Gravenhage (NL)

(72) Inventors: Marc Crockatt, 's-Hertogenbosch (NL); Roman Latsuzbaia, Delft (NL); Johan Urbanus, 's-Gravenhage (NL); Earl Lawrence Vincent Goetheer, Mol (BE); Richard Antonius Van Heck, Leuven (BE)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 296 days.

(21) Appl. No.: 17/414,419

(22) PCT Filed: Dec. 20, 2019

(86) PCT No.: PCT/NL2019/050867
§ 371 (c)(1),
(2) Date: Jun. 16, 2021

(87) PCT Pub. No.: WO2020/130832
PCT Pub. Date: Jun. 25, 2020

(65) Prior Publication Data
US 2022/0090274 A1 Mar. 24, 2022

(30) Foreign Application Priority Data
Dec. 21, 2018 (WO) ................ PCT/NL2018/050881

(51) Int. Cl.
| | |
|---|---|
| C07C 51/21 | (2006.01) |
| C07C 51/29 | (2006.01) |
| C07C 51/305 | (2006.01) |
| C25B 3/07 | (2021.01) |
| C25B 3/23 | (2021.01) |
| C07C 51/235 | (2006.01) |
| C25B 11/04 | (2021.01) |

(Continued)

(52) U.S. Cl.
CPC .............. *C07C 51/235* (2013.01); *C25B 3/07* (2021.01); *C25B 3/23* (2021.01); *C25B 11/04* (2013.01); *C25B 11/042* (2021.01); *C25B 11/052* (2021.01)

(58) Field of Classification Search
CPC .... C25B 3/05; C25B 3/07; C25B 3/23; C07C 51/21; C07C 51/29; C07C 51/305; C07C 51/313
USPC ......... 205/427, 440, 441; 562/523, 524, 527
See application file for complete search history.

(56) References Cited

U.S. PATENT DOCUMENTS

| | | | |
|---|---|---|---|
| 1,709,297 A | 4/1929 | Yabuta | |
| 4,155,920 A | 5/1979 | Milberger et al. | |
| 2015/0316557 A1 | 11/2015 | Keillor et al. | |

FOREIGN PATENT DOCUMENTS

| | | | | |
|---|---|---|---|---|
| CN | 103910699 A | 7/2014 | | |
| CN | 104119219 A | * 10/2014 | ............. | C07C 51/23 |
| CN | 102977244 B | 6/2015 | | |

(Continued)

OTHER PUBLICATIONS

Kubota et al. Electrochemical Valorization of Furfural to Maleic Acid. ACS Sustainable Chem. Eng. 2018, 6, 9596-9600, XP002795187, DOI: 10.1021/ACSSUSCHEMENG.8602698.

(Continued)

*Primary Examiner* — Edna Wong
(74) *Attorney, Agent, or Firm* — Banner & Witcoff, Ltd.

(57) ABSTRACT

The invention is directed to a process for preparing maleic acid or a derivative thereof, the process comprising a step b) of oxidizing 5-hydroxy-2(5H)-furanone and/or cis-β-formylacrylic acid to maleic acid or a derivative thereof by contacting the 5-hydroxy-2(5H)-furanone and/or cis-β-formylacrylic acid with molecular oxygen ($O_2$) in the presence of a catalyst. In a particular embodiment, the step b) is preceded by a step a) of oxidizing a furanic compound according to formula I into the 5-hydroxy-2(5H)-furanone and/or cis-β-formylacrylic acid,

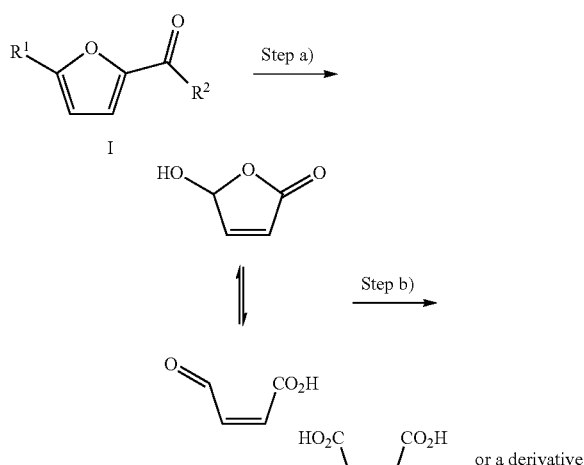

wherein $R^1$ is H, $CH_2OH$, $CO_2H$ or CHO and $R^2$ is H, OH, $C_1$-$C_6$ alkyl or O($C_1$-$C_6$ alkyl), or esters, ethers, amides, acid halides, anhydrides, carboximidates, nitriles, and salts of formula I.

21 Claims, No Drawings

(51) Int. Cl.
C25B 11/052 (2021.01)
C25B 11/042 (2021.01)

(56) References Cited

FOREIGN PATENT DOCUMENTS

| CN | 104119219 B | 8/2016 | |
|---|---|---|---|
| GB | 253877 A | 1/1927 | |
| GB | 297667 A | 5/1929 | |
| JP | 2002-179665 A | 6/2002 | |
| JP | 2013-126967 A | 6/2013 | |
| JP | 2022514771 A | 2/2022 | |
| RU | 2455298 C1 * | 7/2012 | ........... C07D 307/58 |
| WO | 03048097 A1 | 6/2003 | |
| WO | 2010007139 A1 | 1/2010 | |
| WO | 2015060827 A1 | 4/2015 | |
| WO | 2020130832 A1 | 6/2020 | |

OTHER PUBLICATIONS

Maier et al. "Search for Alternative Routes to Tetra-tert-butyltetrahedrane; Synthesis of Sterically Overcrowded Molecules". Liebigs Ann. 1995, 153-160.
Chen et al. "Ring Substituent Effects on the Thiol Addition and Hydrolysis Reactions of N-Arylmaleimides". J. Org. Chem. 2015, 80, 12182-12192.
Loughlin et al. "Total Synthesis of (( )-Hyphodermins A and D" J. Org. Chem. 2008, 73, 3535-3440.
Badovskaya et al. "Rearrangements and Tautomeric Transformations of Heterocyclic Compounds in Homogeneous Reaction Systems Furfural-?2?2-Solvent" Russian Journal of General Chemistry, 2018, vol. 88, No. 8, pp. 1568-1579.
Robert et al. "Facile and Efficient Synthesis of Cyclic Anhydrides from Dicarboxylic Acids". ACS Catal 2014, 4, 3586-3589.
Lan et al. "Transformation of 5-Hydroxymethylfurfural (HMF) to Maleic Anhydride by Aerobic Oxidation with Heteropolyacid Catalysts". ACS CataL 2015, 5, 2035-204.
Tachibana et al. "Synthesis of Biomass-Based Monomers from Biomass-Based Furfural for Polyesters and Evaluation of Their Biomass Carbon Ratios". ACS Symposium Series; American Chemical Society: Washington, DC, 2012. Downloaded by Nanyang Tech Univ Lib on May 30, 2014 | <http://pubs.acs.org>. Publication Date (Web): Aug. 16, 2012 | doi: 10.1021/bk-2012-1105.ch007.
Choudhary et al. "Metal-free oxidative synthesis of succinic acid from biomass-derived furan compounds using a solid acid catalyst with hydrogen peroxide". Applied Catalysis A: General 458 (2013) 55-62.
Li et al. "Pt nanoparticles over TiO2—ZrO2 mixed oxide as multifunctional catalysts for an integrated conversion of furfural to 1,4-butanediol" Applied Catalysis A: General 478 (2014) 252-258.
Fan, Guo-zhi. "Study on the new technology of synthesis of dimethyl fumarate". Applied Chemical Industry, Jun. 2004, vol. 33, No. 3.
Tachibana et al. "Chemical Synthesis of Fully Biomass-Based Poly(butylene succinate) from Inedible-Biomass-Based Furfural and Evaluation of Its Biomass Carbon Ratio" Biomacromolecules, 2010, 11, 2760-2765.
Hjelmgaard et al. "Synthesis of Furanone-Based Natural Product Analogues with Quorum Sensing Antagonist Activity". Bioorganic & Medicinal Chemistry 11 (2003) 3261-3271.
Shi et al. "Synthesis of maleic acid from renewable resources: Catalytic oxidation of furfural in liquid media with dioxygen". Catalysis Communications 12 (2011) 731-733.
Choudhary et al. "Highly Efficient Aqueous Oxidation of Furfural to Succinic Acid Using Reusable Heterogeneous Acid Catalyst with Hydrogen Peroxide" Chem. Lett. 2012, 41, 409-411.
Badovskaya et al. "Catalytic Oxidation of Furan and Hydrofuran Compounds. 7. Production of 2(5H)-Furanone by Oxidation of Furfural with Hydrogen Peroxide and Some of Its Transformations in Aqueous Solutions" Chemistry of Heterocyclic Compounds 38, 1040-1048 (2002).
Casanova et al. "Biomass into chemicals: one pot-base free oxidative esterification of 5-hydroxymethyl-2-furfural into 2,5-dimethylfuroate with gold on nanoparticulated ceria". Journal of Catalysis 265 (2009) 109-116.
Menegazzo et al. "On the process for furfural and HMF oxidative esterification over Au/ZrO2". Journal of Catalysis 319 (2014) 61-70.
Menegazzo et al. "Structure-activity relationships of Au/Zr02 catalysts for 5-hydroxymethylfurfural oxidative esterification: Effects of zirconia sulphation on gold dispersion, position and shape". Journal of Catalysis 326 (2015) 1-8.
Milas, Nicholas. "Catalytic Oxidations in Aqueous Solutions. I. The Oxidation of Furfural". Catalytic Oxidations, Aug. 1927.
Poskonin, V.V. Catalytic Oxidation Reactions of Furan And Hydrofuran Compounds 9. Characteristics And Synthetic Possibilities of the Reaction of Furan with Aqueous Hydrogen Peroxide in the Presence of Compounds of Niobium(Ii) and (V). Chemistry of Heterocyclic Compounds, vol. 45, No. 10, 2009.
Alonso-Fagundez et al. "Selective Conversion of Furfural to Maleic Anhydride and Furan with VOX/A1203 Catalysts" ChemSusChem 2012, 5, 7984-1990.
Deng et al. Aerobic Oxidation of Hydroxymethylfurfural and Furfural by Using Heterogeneous Cox0y-N@C Catalysts. ChemSusChem. Chemistry & Sustainability, Energy & Materials. Copyright Wiley-VCH Verlag GmbH & Co. KGaA, 69451 Weinheim, 2014.
Zhao et al. "Use of submerged anaerobic-anoxic-oxic membrane bioreactor to treat highly toxic coke wastewater with complete sludge retention". Journal of Membrane Science, vol. 330, Issues 1-2, Mar. 20, 2009, pp. 57-64.
Gassama et al. "Synthesis of surfactants from furfural derived 2[5H]-furanone and fatty amines". Green Chem., 2010, 12, 859-865.
Tachibana et al. "Synthesis and characterization of a renewable polyester containing oxabicyclic dicarboxylate derived from furfural". Green Chem., 2013, 15, 1318.
Badovckaya, L.A. "New Reaction for the Preparation of Lower Oxodihydrofurans". Krasnodar Polytechnic Institute, Krasnodar 35006. Translated from Khimiya Geterotsiklicheskikh Soedinenii. No. 10, pp. 1314-1319, Oct. 1978. Original article submitted Dec. 1, 1976, revision submitted Mar. 31, 1978.
Milman, et al. "Effect of homogeneous catalysts on the electrochemical synthesis of b-formylacrylic acid". Elektrokhimiya, vol. 14, Issue: 10, pp. 1555-1558, Journal, 1978, Coden: Elkkax, ISSN: 0424-8570.
Milman et al. "Determination of the Parameter of Electrochemical Furfural Oxidation at a carbon electrode in a continuous cell" Soviet Electrochemistry, 1986, vol. 22, No. 12. p. 1539.
Kemppainen et al. "Mukaiyama-Michael Reactions with Acrolein and Methacrolein: A Catalytic Enantioselective Synthesis of the C17—C28 Fragment of Pectenotoxins". Organic Letters 2012, vol. 14, No. 4, 1086-1089.
Song et al. "Asymmetric Total Syntheses of (−)-Penicipyrone and (−)-Tenuipyrone via Biomimetic Cascade Intermolecular Michael Addition/Cycloketalization" Organic Letters 2013, vol. 15, No. 1, 6-9.
Cao et al. "A Convenient Synthesis of 2(5H)-Furanone" Organic Preparation and Procedures International: The New Journal for Organic Synthesis, 28:2, 2015-216, DOI:10.1080/00304949609356524.
Nasman, Jan. "3-Methyl-2(5H)-Furanone". Organic Syntheses, Publication of Reliable Methods for the Preparation of Organic Compounds. Coll. vol. 8, p. 396 (1993); vol. 68, p. 162 (1990).
Milas, Nicholas. "Fumaric Acid". Organic Syntheses.
Alonso-Fagundez et al. "Aqueous-phase catalytic oxidation of furfural with H20 2: high yield of maleic acid by using titanium silicalite-1". RSC Adv., 2014, 4, 54960.
Badovskaya et al. "Effect of Acid-Base Properties of the Medium on the Reactions in the 2-Furaldehyde-H2O2—H2O System with and without VOSO4" Russian Journal of General Chemistry, 2014, vol. 84, No. 6, pp. 1133-1140.

(56) References Cited

OTHER PUBLICATIONS

Tachibana et al. "Synthesis and Verification of Biobased Terephthalic Acid from Furfural" Scientific Reports, 5: 8249, DOI: 10.10313/srep013249.

Anders et al. "An Improved One-Pot Preparation of 2-Furanones"Synthesis, Communication, 19885, pp. 786-788.

Wojcieszak et al. "Recent developments in maleic acid synthesis from bio?based chemicals". Sustain Chem Process (2015) 3:9 DOI 10.1186/s40508-015-0034-5.

Hellstrom, Av Nils. "Om elektrolytisk oxidation av furfurol".

Salles et al. "A Self-Organizing Chemical Assembly Line". J. Am Chem. Soc 2013, 135, 19143-19146.

Barbosa et al. "Phytogrowth Activity of 3-(3-Chlorobenzyl)-5-arylidenefuran-2(5H)-ones". Z. Naturforsch. 2009, 64b, 245-251.

* cited by examiner

OXIDATION OF 5-HYDROXY-2-FURANONE TO MALEATES

RELATED APPLICATIONS

This application is a National Stage Application under 35 U.S.C. 371 of co-pending PCT application PCT/NL2019/050867 designating the United States and filed Dec. 20, 2019; which claims the benefit of PCT application number PCT/NL2018/050881 and filed Dec. 21, 2018, each of which are hereby incorporated by reference in their entireties.

The invention is in the field of the chemical preparation of maleic acid and derivatives thereof. In particular, the invention is directed to a sustainable chemical preparation of maleic acid and derivatives thereof using starting materials derivable from biomass.

Current industrial processes for the production of maleic acid are typically based on the hydrolysis of maleic anhydride, which itself is produced by oxidation of petrochemicals such as butane or benzene. It is desired to replace petrochemicals with chemicals that are based on biomass in order to reduce the environmental footprint of the production and to provide a more sustainable route to maleic acid, see e.g. Wojcieszak et al., *Sustainable Chemical Processes*, 2015, 3:9, 1-11

For instance, in *Journal of Organic Chemistry*, 1986, 51(4), 567-569; the chemical oxidation of furfural, a biomass-derivable chemical, with hydrogen peroxide is disclosed. The use of hydrogen peroxide for the oxidation of furfural into maleic acid is also reported in Badovskaya et al. *Russian Journal of General Chemistry*, 2018, 88(8), 1568-1579. A drawback of such chemical oxidation reactions is the requirement of hydrogen peroxide as the oxidation agent, as this must be prepared in a separate production process, is relatively expensive and is consumed in the reaction. As such, the overall advantage of using a biomass-derivable chemical is reduced.

Alternatively, the furfural may be oxidized electrochemically, as is disclosed in GB253877, Mil'man et al., *Elektrokhimiya*, 1978, Volume: 14, Issue: 10, 1555-1558 and Hellström: *Svensk Kemish Tidskrift*, 1948, Volume 60, 214-220. However, a drawback of both these known methods for preparing maleic acid is i.a. that furfural is used as the starting material, and the one-pot oxidation process is time consuming and typically requires the presence of a mediator to achieve acceptable reaction rates. Mediators however, add expense and are often difficult to recycle, and therefore generally not preferred in large scale procedures.

It is desired to provide a process to prepare maleic acid in a high atom-efficiency from biomass, in particular from biomass-originating furanic compounds.

The present inventors found that in certain oxidative processes, e.g. in electrochemical processes of furanic compounds, the tautomers 5-hydroxy-2(5H)-furanone (herein also referred to as HFO and cis-β-formylacrylic acid (also referred herein as formyl-acrylic acid) are formed as intermediates.

Scheme 1

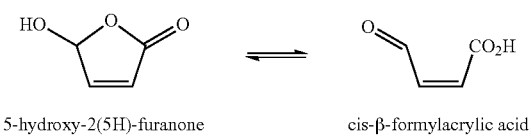

5-hydroxy-2(5H)-furanone ⇌ cis-β-formylacrylic acid

Without wishing to be bound by theory, it is believed that the closed ring form (i.e. the 5-hydroxy-2(5H)-furanone) cannot, or can only very slowly, be electrochemically oxidized and that as such, this oxidation is hampered. At various circumstances and conditions, the equilibrium lies almost completely at the side of the furanone, so slow reaction may occur, in particular in an atom-efficient electrochemical oxidation process. Although this slow reaction may be overcome by chemical oxidation reactions with hydrogen peroxide, the use of this hydrogen peroxide is not preferred for i.a. the reasons mentioned herein-above.

The present inventors have however surprisingly found that 5-hydroxy-2(5H)-furanone and/or cis-β-formylacrylic acid can be oxidized to maleic acid or a derivative thereof by molecular oxygen ($O_2$), also referred to as oxygen.

Accordingly, the present invention is directed to a process for the preparation of maleic acid or a derivative thereof, said process comprising a step of oxidizing 5-hydroxy-2(5H)-furanone and/or cis-β-formylacrylic acid to maleic acid or a derivative thereof by contacting 5-hydroxy-2(5H)-furanone and/or cis-β-formylacrylic acid with molecular oxygen ($O_2$) in the presence of a catalyst, said step herein referred to as step b).

The inventors have found that several metals, in particular transition metals can suitably catalyze the oxidation reaction in step b). Particular good results were obtained with copper, gold, palladium, platinum and ruthenium, especially gold.

The catalyst preferably further comprises a solid support. The solid support may be a support known in the art and generally any support may be suitable, provided that it is not detrimental to the oxidation reaction. Typically, the solid support is inert in step b). Examples of support that we found to be suitable for the present invention include activated carbon, aluminum oxide, zinc oxide, and titanium dioxide. Titanium dioxide as a solid support, in particular in combination with gold gave particular good results in term of maleic acid yield.

Step b) of the present invention is generally carried out in a liquid and not in a gaseous phase. Due to the instability of furanic compounds and of HFO at the high temperatures which are required to maintain the compounds in gaseous form, gaseous phase reaction conditions are not well suitable for the present invention. It is accordingly preferred that the HFO and/or formyl-acrylic acid is/are liquid or dissolved in a solvent when contacted with $O_2$. Suitable solvents include both organic and aqueous solvents. For reasons elaborated herein-below, water-immiscible organic solvents and acidic aqueous solvents are particularly preferred. Good conversion of HFO and/or formyl-acrylic acid was obtained in water, aqueous sulfuric acid, acetic acid, ethyl acetate, methyl isobutyl ketone (MIBK), methyl tert-butyl ether (MTBE), 2-methyl tetrahydrofuran (2-MeTHF), dichloromethane, heptane, acetonitrile, acetone, nitromethane and toluene, preferably 2-MeTHF, toluene and MTBE.

The solvent in which step b) may be carried out, can have an influence on the product that is formed. For instance, in organic solvents, maleic anhydride may be formed by an in situ dehydration reaction of maleic acid or when HFO is directly oxidized by the catalyst. At the other hand, in an aqueous solvent, maleic acid itself is typically formed under acidic conditions, while a salt of maleic acid can be formed under basic conditions. Under certain reaction conditions, maleic acid may also, at least partially, isomerize to fumaric acid. The reaction conditions under which step b) is carried out, typically also influence the product that is formed.

The oxidation process was found to give the best results in terms of conversion under moderate reaction conditions, including slightly elevated temperature and pressure. Accordingly, step b) is preferably carried out under a pressure of at least 5 bar, preferably at least 10 bar. Preferred temperature ranges to carry out step b) are 20 to 200° C., more preferably in 50 to 150° C., most preferably 60 to 100° C. These conditions allow the reaction to be carried out in a continuous reaction, such as a tube reactor, which is preferred. The reactor may accordingly comprise a fixed catalyst bed comprising the catalyst.

The starting materials HFO and/or formyl-acrylic acid can be supplied or provided in step b) in an isolated (i.e. essentially pure) formulation or in a reaction mixture that originating from a preceding process. The isolated formulation can be obtained by a preceding process and isolation that is not part of the present invention. This preceding reaction can be any type of reaction process and could for instance have served to produce HFO and/or formyl-acrylic acid as main products, or HFO and/or formyl-acrylic acid could have been produced therein as side products. In a preferred embodiment of the present invention, HFO and/or formyl-acrylic acid originate from one or more furanic compounds having a biomass origin.

Details on Step a)

In a preferred embodiment as illustrated in Scheme 2, step b) is preceded by a step a) of oxidizing a furanic compound according to formula I into 5-hydroxy-2(5H)-furanone and/or cis-β-formylacrylic acid, wherein $R^1$ is H, $CH_2OH$, $CO_2H$ or CHO and $R^2$ is H, OH, $C_1$-$C_6$ alkyl or $O(C_1$-$C_6$ alkyl), or esters, ethers, amides, acid halides, anhydrides, carboximidates, nitriles, and salts thereof.

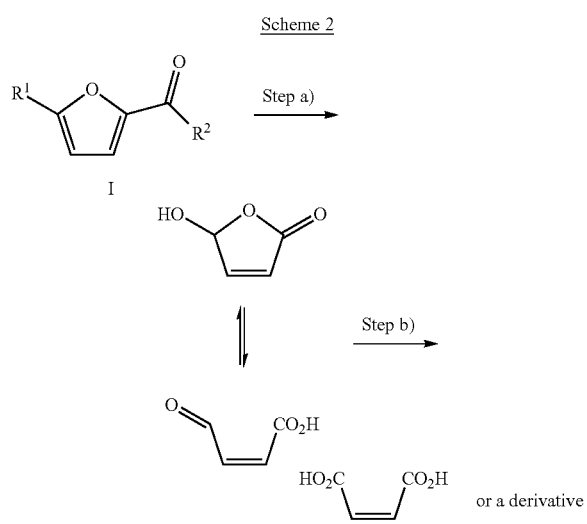

Scheme 2

The electrochemical oxidation of the furanic compound according to formula I is described in detail in PCT/NL2018/050881, which is incorporated herein in its entirety. It was found that carrying out step b) in accordance with the present invention in combination with the electrochemical oxidation of the furanic compound is especially beneficial, as it was found that a preferred pH of the electrochemical oxidation, the equilibrium between HFO and formyl-acrylic acid lies almost completely at the side of the HFO, so slow oxidation occurs. Although an acceptable reaction rate in the electrochemical oxidation can be achieved by applying a mediator, the presence of a mediator however is particularly on a large scale not preferred. Typical mediators are costly and large-scale processes would require recycling or immobilization of the mediator for the process to be economically feasible. Step b) according to the present invention shows good reaction of HFO and formyl-acrylic acid and as such, a two-step process including steps a) and b) is overall preferred.

In a preferred embodiment, the furanic compound comprises 2-furoic acid compound or esters thereof because this is advantageously more stable than furfural and can be available as a side-product in the production of 2,5-furandicarboxylic acid (FDCA) or obtained by stabilization of furfural by direct oxidation to furoic acid, which is generally a process at mild conditions (e.g. at reaction temperature of less than 100° C.). As such, the use of a 2-furoic acid compound is preferred. Moreover, the application of furoic acid in chemical processes in accordance with the present invention is also beneficial since it is believed that there are currently no significant markets envisaged for furoic acid.

It was found that the use of furoic acid to produce maleic acid and the replacement of furfural by furoic acid, is particularly advantageous in electrochemical oxidation reaction. Electrochemical reactions tend to have significantly longer residence times than thermochemical reactions (due to limitations in the surface area of the electrodes, and mass transfer to/from the surface, vide infra), so the chemical materials are often a lot longer in solution where they are prone to decompose. Therefore, the electrochemical oxidation process to prepare maleic acid benefits particularly from an increase stability of the starting material. Accordingly, the oxidation comprises, or for the first aspect preferably consists of, an electrochemical oxidation in an electrolyte solution, typically an aqueous electrolyte solution comprising said furoic acid compound. As such the addition of an oxidation agent such a hydrogen peroxide may not be required. Typically, said process comprises dissolving a furoic acid compound in the electrolyte solution, followed by the electrochemical oxidation to convert said furoic acid or derivative thereof into maleic acid.

In yet another preferred embodiment, the furanic compound comprises furfural. Advantageously, in situ electro-oxidation to 2-furoic acid is simple and fast and can be performed at ambient temperature, so decomposition of furfural can be limited. Furfural has also got good solubility in water (about 83 g/L). Furthermore, starting with furfural saves one overall processing step. Starting with furfural is particularly preferred in scaling up the process of the present invention.

A particular embodiment of the present invention comprises chemo-catalytic oxidation of furfural to furoic acid, prior to carrying out the electrochemical oxidation of furoic acid. With the furoic acid compound is meant any compound that is based on 2-furoic acid and has the same oxidation state as furoic acid such that it can be oxidized to maleic acid. Examples of suitable furoic acid compounds include 2-furoic acid, furoic acid esters, furoic acid amides, furonitrile, anhydrides of furoic acid, carboximidates of furoic acid, furoic acid halides and salts of furoic acid. In particular because of its good solubility in water (about 37.1 g/L in water at 15° C. and about 100 g/L in water at 50° C.), 2-furoic acid is preferably used as the furoic acid compound.

The electrochemical oxidation according to step a) of the present invention is preferably carried out using one or more working electrodes (herein also referred to as the anodic electrode, anode or simply the electrode) comprising lead oxide, for instance $PbO_2$ which lead oxide may optionally supported on a metal such as Pb, a porous graphite such as activated carbon, carbon nanotubes (CNT), reticulated vitreous carbon (RVC), carbon felt or a titanium support, or boron doped diamond (BDD). Activity of the electrode may be improved by adding dopants or adatoms (to the electrode or electrolyte). For instance, addition of metal ions such as $Fe^{2+}$ or $Fe^{3+}$ into the electrolyte can improve stability of $PbO_2$. In principle any electrode structure may be used, including 2D and 3D structures, but one or more electrodes comprising one or more porous electrodes, fusion electrodes, mesh electrodes, nanostructured electrodes, metal or metal oxide particles supported on porous carbon/graphite electrodes or a combination thereof are preferred. Such an electrode results in higher conversion rates. In a particular embodiment, the working electrode may alternatively or additionally comprise one or more of mixed metal oxide (MMO), dimensionally stable anodes (DSA), stainless steel, brass-carbon based graphitic electrodes, boron doped diamond (BDD), Mn (e.g. $MnO_2$), Pt, Au, Ag, Cu, Ir, Ru, Pd, Ni, Co, Zn, Cd, In, Sn, Ti, Fe and alloys or oxides thereof.

The counter electrode (also referred to as cathodic electrode or cathode) may comprise one or more materials selected from the group consisting of Au, Pt, Pd, Ir, Ru, Ni, Co, stainless steel, Cu, Carbon, Pb, Ti or alloys thereof.

In an embodiment, the working electrode is doped with a mediator. The inventors surprisingly found that a vanadium-doped electrode is particularly suitable for carrying out this process. Accordingly, the vanadium-doped electrode is another aspect of the present invention. In this embodiment, it is preferred that the pH of the electrolyte solution is in the range of 3 to 7, more 4 to 5 to limit leaching of the vanadium. Also, $V_2O_5$ in combination with $PbO_2$ can suitably be used, wherein $V_2O_5$ is kept soluble in the electrolyte. It is preferred to have the catalyst, $V_2O_5$, attached to the support, for recycling purposed. Moreover, $PbO_2$, doping of $PbO_2$ by cations (e.g. $Fe^{3+}$, $Co^{2+}$ and $Ni^{2+}$), by $F^-$ or by cations and $F^-$ simultaneously can be a way of improving the stability of electrode and electrochemical activity in processes occurring at high potentials.

The oxidation of the furanic compound can be carried out directly at the electrode. This means that the electrons from the oxidation agent or electrode are directly transferred to the furanic compound or a chemical intermediate in the reaction. Alternatively, the oxidation can be carried out by using a mediator that is reduced or oxidized on the electrode surface, after which it reacts with the target compound in the bulk of the electrode. Although, the presence of the mediator may not exclude oxidation at the electrode, the oxidation typically predominantly proceeds through the mediator if this is present. Preferably the mediator comprises one or more of vanadates, vanadium oxides (e.g. $V_2O_5$, $VO_2$), molybdates ($MoO_4^{2-}$), chromates ($CrO_4^{2-}$), dichromates ($Cr_2O_7^{2-}$), permanganates ($MnO_4^-$) manganates ($MnO_4^{2-}$), manganese salts ($Mn^{2+}$), tungstates ($WO_4^{2-}$), iodates ($IO_3^-$), chlorates ($ClO^-$), chloride-chlorine couple ($Cl^-/Cl_2$), bromates ($BrO^-$), bromide-bromine couple $Br^-/Br_2$, peroxydisulfates ($S_2O_8^{2-}$) ozone ($O_3$), cobalt salts ($Co^{2+}/Co^{3+}$), cerium salts ($Ce^{3+}/Ce^{4+}$), and the like. Most preferably, the mediator comprises vanadium oxide, sodium molybdate, and/or potassium dichromate.

The mediator may be immobilized, e.g. in the close vicinity or at the working electrode. Nevertheless, drawbacks of immobilization remain probably leaching of the mediator and the fact that immobilization limits the amount of mediator available (since the surface area of any support would be limited), which would also limit the rate on large scale Surprisingly, it was found by the present inventors that the oxidation reaction also proceeds satisfyingly without any mediator being present. For reasons of costs, safety issues (mediators are often highly toxic/carcinogenic), increased process complexity (recapturing/recycling of the mediator), and the environmental footprint of the process, it may be preferred that the process is carried out without said mediator. Accordingly, the electrolyte solution is preferably essentially free of said mediator during the electrochemical oxidation. In the context of the present invention, essentially free means preferably less than 5 mol %, preferably less than 1 mol %, more preferably less than 0.01 mol % based on the amount of furanic compound starting material present at the start of the electrochemical oxidation reaction. Most preferable, the electrolyte solution comprises trace amounts or less of the mediator. With "at the start of the electrochemical oxidation reaction" is meant the moment just before the first amount of furanic compound will be oxidized.

The oxidation in step a), in particular the electrochemical oxidation, proceeds particularly well at a certain pH-range. The specifically preferred pH-range can i.a. depend on the used electrode or the oxidation agent, but the $pK_a$-values of the furanic compound may also partially determine the preferred pH-range. In particular when the furanic compound comprises 2-furoic acid, the electrochemical oxidation is preferably at least partially carried out at a pH of less than 7, more preferably less than 4, even more preferably less than 3, most preferably about equal or less than 2.

Due to the conversion of the furanic compound into formyl-acrylic acid, the pH of the electrolyte solution may drop below its value as it was at the start of the reaction. Therefore, it may be possible to start the electrochemical oxidation at a pH-value above the optimal value at which the oxidation can be carried out and that during the conversion of the furanic compound, the pH-value decrease to the optimal pH-value or to the preferred pH-values as defined above. Therefore, the preferred pH-values are defined for at least part of the duration of the electrochemical oxidation (vide supra: "at least partially carried out at a pH of . . . ") and not necessarily for the entire duration of the electrochemical oxidation. In certain embodiments however, concentrated sulfuric acid is used as electrolyte and the change of pH may typically be very little.

The pH can be adjusted from an external source during the process to maintain the optimal pH during the whole reaction (e.g. addition of a suitable acid or base). Furthermore, it might also be carried out in the presence of a buffer to maintain pH. In addition, the desired pH-range can be set by using an appropriate solvent or appropriate electrolyte solution. Accordingly, it is preferred that the solvent or electrolyte solution, if present, comprises an acid such as an organic and/or a mineral acid. A mineral acid is preferred since, compared to organic acids, mineral acids are more inert in the electrochemical oxidation reaction and therefore preferred. More preferably, the mineral acid is selected from the group consisting of hydrochloric acid (HCl), nitric acid ($HNO_3$), phosphoric acid ($H_3PO_4$), sulfuric acid ($H_2SO_4$), boric acid ($H_3BO_3$), hydrofluoric acid (HF), hydrobromic acid (HBr), perchloric acid ($HClO_4$), hydroiodic acid (HI). Most preferably the electrolyte solution comprises sulfuric acid, as persulfates could be formed on $PbO_2$ electrodes when oxidation potential is applied to it. Persulfates are also strong oxidants. In certain embodiments, the acid can be at least partially immobilized by incorporating it into a resin (such as Amberlyst™ or Nafion™), which could be added to the mixture, and/or the acid can be structurally incorporated into the one or more electrodes. In certain embodiments, it may be preferred that the electrolyte comprise the acid in combination with an inorganic salt to increase the ionic conductivity of the electrolyte. For instance, if the pH of the electrolyte is desired to be 1, the concentration of the acid may not be sufficient to provide good conductivity and the additional of salt to that end may be preferred.

The electrolyte solution can be aqueous or non-aqueous. Suitable non-aqueous electrolyte solutions comprise one or more solvents selected from the group consisting of acetone, sulfolane, dimethylsulfoxide (DMSO), tetrahydrofuran (THF), dimethylformamide (DMF), N-methylpyrrolidone (NMP), hexamethylphosphoricacid-triamide (HMPA), acetonitrile (MeCN), dichloromethane (DCM), propylene carbonate, hexafluoroisopropanol (HFIP), and ionic liquids (for instance [C4mim]$^+$) with anions $HSO_4^-$, $CF_3CO_2^-$, $H_2PO_4^-$, $Cl^-$, $NO_3^-$, $BF_4^-$, $OTf^-$, $PF_6^-$). In particular for the embodiments wherein the solvent is not an ionic liquid, it is preferred that the non-aqueous electrolyte solution comprises an inorganic or organic salts as electrolyte.

To increase the conversion rate of the furanic compound to the HFO and/or formyl-acrylic acid, it may be preferable that the electrochemical oxidation is carried at a temperature in the range of 10 to 100° C., more preferably in the range of 15 to 70° C. In particular for electrochemical oxidation, it is not common to carry out the oxidation at elevated temperatures (i.e. above room temperature). However, for the present process, it was found that elevated temperatures and in particular temperatures of about 35 to 60° C. do result in an increased conversion rate and yield as well better solubility (i.e. concentration can be increased somewhat). In the case that the furanic compound comprises furfural, its electrochemical oxidation to HFO and/or formyl-acrylic acid is preferably carried out in the range of 20° C. to 50° C. when the mediator such as $V_2O_5$ is present. In the absence of the mediator, a temperature about room temperature is preferred (e.g. about 17 to 23° C.).

Although a high concentration of the starting material in the reaction solvent is typically advantageous to achieve a high conversion rate in chemical redox reactions, this is may be less the case for electrochemical oxidation reactions since the rate can be limited by the electron density at the electrode and less by the concentration of the reactants in the solution. In other words, the accessible electrode surface area and the electrical current mostly influence the conversion rate. Although a high concentration of the starting material in the reaction solvent is typically advantageous to achieve a high conversion rate in chemical redox reactions, this is may be less the case for electrochemical oxidation reactions. Generally, in such processes, increasing concentration increases the electrical current until the value of the kinetic electrical current, which is determined by the nature of electrode, the surface area of the electrode, the molecule(s) to react, adsorption properties on the electrode and the like. Then the reaction cannot proceed faster. It becomes limited by the exchange of formed product at the electrode with fresh reactant. In other words, the accessible electrode surface area, the electrical current, and the mass transfer typically mostly influence the conversion rate. Therefore, a higher concentration may not necessarily result in an increased reaction rate, and might only result in long reaction times, which may in turn lead to decomposition of reactant(s), intermediates, or product(s). This is particularly undesired for continuous flow reactions wherein full conversion may as such not be reached. Therefore, in the embodiments wherein the process comprises the electrochemical oxidation, it is preferred that the electrochemical oxidation is carried out at a concentration of the furanic compound in the electrolyte solution in the range of 0.01 to 5 mol/L, preferably in the range of 0.1 mol/L to 3.5 mol/L, more preferably in the range of 0.3 mol/L to 2 mol/L. This range gave particular good conversion rates and yields. Since the concentration may decrease in time, with concentration is herein meant the initial concentration of the furanic compound, i.e. the concentration at the start of the reaction.

In a preferably embodiment, the electrochemical oxidation is carried out in a two-compartments electrochemical cell in which the anode electrolyte solution and the cathode electrolyte solution are separated by a membrane (e.g. a semi permeable membrane such as a cation exchange membrane (CEM) or anion exchange membrane (AEM) depending on the specifics of the process). This embodiment is particularly preferable for carrying out the process on large scale as it will prevent the reaction product (i.e. HFO and/or formyl-acrylic acid) being reduced at the cathode, and also because it will prevent or at least limit the furanic compound from crossing over to the cathode, in both which cases efficiency would be reduced. Suitable membranes for this embodiment include membranes available under the tradenames Nafion™, Fumatech™, Neosepta™ and/or Selemion™ and the like. Also, a porous diaphragm/glass frit might be sufficient.

Advantageously, the present process may also comprise paired electro-synthesis to enable co-currently an electrochemical reduction, e.g. production of hydrogen from water, reduction of oxygen to water, or conversion of furfural to furfuryl alcohol, at the cathode. It may also be possible to reduce oxygen to water in order to reduce cell voltage and energy consumption.

It may be appreciated that the present electrochemical oxidation is particularly preferred to minimize chemical waste formation. Chemical waste formation can be further suppressed by carrying out the process of the present invention with an electrolyte solution that consists essentially of water, the furanic compound, the acid (as the electrolyte) and possible reaction intermediates and products such as the HFO and/or formyl-acrylic acid. In other words, although possible, the presence of additives such as salts, stabilization agents, buffers, surfactants and the like is not preferred and the electrolyte solution is preferably free of such additives. An additional advantage of not including a salt in the electrolyte solution is that the HFO and/or formyl-acrylic acid can directly be obtained as the free acid, and not necessarily as the salt thereof. In step b), the free acid is typically preferred.

Alternative to the electrochemical oxidation, the furanic compound can also be oxidized in step a) in a photochemical reaction, for instance as described by Galles et al. *J. Am Chem. Soc.* 2013, 135, 19143-19146. Such an oxidation of furfural is for example described in Synthesis 2012, 44 (16), 2560-2566 and CN108314647. A photochemical oxidation of 2-furoic acid is for example described in Catalysis Communications 2010, 11(13), 1081-1084; *Tetrahedron Letters* 2010, 51(26), 3360-3363; Synthesis 2009, (11), 1791-1796; Chemistry Letters 2004, 33(9), 1142-1143; 2004 and *Bull. Chem. Soc. Japan* 2006, 79(12), 1983-1987.

The photochemical oxidation of the furanic compound is preferably carried out in an organic solvent such as $CHCl_3$, THF, MeOH, and the like.

Solvents of Step a) and b)

In case the step a) is carried out in an aqueous electrolyte solution (which is preferable), step b) can be carried out in the same solution, in the same solution but after a shift in pH, or after extraction of the HFO and/or formyl-acrylic acid with an organic solvent, preferably a water-immiscible organic solvent. For the latter embodiment, it is preferable to carry out step b) in the same type of organic solvent that was used for the extraction. It may be appreciated that this embodiment covers processes in which the organic extraction is subjected to intermediate drying, and those in which it is not dried before further use. Examples of water-immiscible organic solvents that can be used include dichloromethane, toluene, ethyl acetate, 2-methyltetrahydrofuran and the like. In this particular embodiment, maleic anhydride may be obtained directly from the process without a separate subsequent dehydration step. It may also be possible to carry out step b) in an alcoholic solvent such as methanol or ethanol to get the mono and/or di-ester of maleic acid directly.

In an embodiment of the present invention comprising steps a) and b) being carried out in the same solution, the process further comprises a step of isolating the maleic acid or the derivative thereof to provide the isolated maleic acid or derivative thereof, and a used electrolyte solution. The used electrolyte solution can then be recycled into the process. The used electrolyte solution may contain residual furanic compound, intermediates of the process, maleic acid, and any other impurities and/or polymers that are formed. Accordingly, it may be preferred to purify the used electrolyte solution prior to recycling (e.g. nano-filtration to remove polymeric materials). Alternatively or additionally to the purification, it may be preferred to bleed some of the recycled electrolyte and add fresh material to maintain a constant quality of the electrolyte.

Isolation of the maleic acid or the derivative thereof can be carried out using standard isolation techniques such as distillation and the like. The specifically preferred method of isolation may depend on the used solvent. By isolation of the maleic acid, the pH of the electrolyte solution can also be restored to the original pH, i.e. the pH at the start of the oxidation. As such, no pH adjustment by additives may be required. In case some electrolyte, acid, solvent or water is lost or consumed during the oxidation of the furanic compound or the isolation of the maleic acid, the acid, solvent or water can be replenished during the recycling of the electrolyte solution.

Recycling of the electrolyte solution is particularly preferred when the present process is a continuous process and for instance carried out in a continuous reactor system. The reactor system in which the process is carried out can accordingly comprise a recycle loop for the electrolyte solution. Recycling the electrolyte solution may advantageously result in a minimal chemical waste production and a reduced external input.

A further embodiment of the present invention comprises a step of further reacting the maleic acid. Derivatives of maleic acid that can be obtained in the step of further reacting the maleic acid may comprise fumaric acid, succinic acid, and salts, esters, anhydrides, amides or imides thereof. This optional further reaction step to provide maleic anhydride, fumaric acid, succinic acid or salts, esters or anhydrides thereof as such (i.e. without the preceding oxidation of furanic compound) is known in the art. For instance, maleic anhydride, fumaric acid and succinic acid can be obtained from maleic acid via a dehydration reaction, an isomerization reaction and a partial hydrogenation reaction, respectively. Fumaric acid is currently produced (predominantly) on an industrial scale by the catalytic isomerization of maleic acid. Succinic acid is also produced industrially from partial reduction of maleic acid, although this is one of several known routes.

In a preferred embodiment of the present invention, the process further comprises a step of isolating the maleic acid or the derivative thereof to provide the isolated maleic acid or derivative thereof.

As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features.

For the purpose of clarity and a concise description features are described herein as part of the same or separate embodiments, however, it will be appreciated that the scope of the invention may include embodiments having combinations of all or some of the features described. The present invention can be illustrated by the following non-limiting examples.

EXAMPLE 1: CONVERSION OF FURFURAL TO 5-HYDROXY-2(5H)-FURANONE

The anode compartment of an H-cell was charged with 100 mL of 0.5 M aqueous sulfuric acid containing 50 mM of furfural. Conversion at 20° C. The cathode compartment of the H-cell was charged 100 ml of 0.5 M aqueous sulfuric acid. A 10 cm$^2$ PbO$_2$ electrode was activated by CV between 0.5-2,1V against SHE. The reference and working electrodes were made ready then a potential of 1.85 V vs. SCE was applied across the cell. Analysis after 7 hours shows ~2:1 ratio of the reaction intermediate formyl-acrylic acid:maleic acid present, and ~9:1 after 20 hours. The maximum total yield of the product (maleic acid and 5-hydroxy-2(5H)-furanone is ~80%).

EXAMPLE 2: EXTRACTION OF CIS-3-FORMYLACRYLIC ACID/5-HYDROXY-2(5H)-FURANONE AND MALEIC ACID FROM ELECTROLYTE

An equal volume of an electrolyte containing formyl-acrylic acid:maleic acid present in a ratio of about 1:10 and an organic solvent (Ethyl acetate, Dichloromethane, Toluene, 2-Methyltetrahydrofuran, Diethyl Ether) were mixed together intensely and then left to phase separate. Both the aqueous and organics phases were then analysed by HPLC to determine the relative levels of cis-β-formylacrylic acid/5-hydroxy-2(5H)-furanone and maleic acid in each of the phases:

|  | Aqueous Phase | | Organic Phase | |
| --- | --- | --- | --- | --- |
|  | Furanone | Maleic Acid | Furanone | Maleic Acid |
| Ethyl Acetate | 8.3% | 54.8% | 91.7 | 45.2% |
| Dichloromethane | 99.1% | 100% | 0.9% | 0% |
| Toluene | 99.1% | 100% | 0.9% | 0% |
| 2-MethylTHF | 41.3% | 26.4% | 58.7% | 73.6% |
| Diethyl Ether | 65.9% | 63.2% | 34.1% | 36.6% |

The conditions using ethyl acetate were scaled up, with the organic phase being separated from the aqueous, dried over sodium sulfate, then concentrated in vacuo to yield a white solid product (400 mg). This was analyzed by NMR and confirmed to be a ~2.7:1 ratio of cis-β-formylacrylic acid/5-hydroxy-2(5H)-furanone:maleic acid.

EXAMPLE 3: CONVERSION OF FURFURAL TO 5-HYDROXY-2(5H)-FURANONE

To tow separate reactors were charged the cis-β-formylacrylic acid/5-hydroxy-2(5H)-furanone:maleic acid mixture (50 mg), 5% palladium on carbon (25 mg), and solvent (350 μL—either 0.5M aqueous sulfuric acid or a pH 7 aqueous buffer solution of monopotassium phosphate and dipotassium phosphate). The reactors were then heated to 70° C. with stirring and oxygen was bubbled through the mixture. After 2 hours, the reactions were cooled to room temperature and analyzed by HPLC. In both cases, conversion of cis-β-formylacrylic acid/5-hydroxy-2(5H)-furanone to maleic acid was observed.

EXAMPLE 4: SOLVENTS FOR THE OXIDATION OF HFO TO MALEIC ACID

An autoclave (10 ml) was charged with HFO, solvent (1 ml) and 10% Pd/C according to the Table 1 below.

The reactor was sealed then flushed with nitrogen. The reactor was then charged to 10 bar of pressure with pure oxygen. The reactor was then heated to 85° C. and stirred for 15 hours. After cooling to ambient temperature, the pressure was released and the reactor flushed with nitrogen. The product solutions were then filtered to remove catalyst, then analyzed by high-performance liquid chromatography (HPLC), with the yield of maleic acid compiled in Table 1.

TABLE 1

| Solvent | HFO (mg) | Pd/C (mg) | TOF/sec for MA* |
|---|---|---|---|
| Water | 10.0 | 5.7 | 0 |
| 0.5M Sulfuric Acid | 8.3 | 4.1 | 0 |
| Ethyl Acetate | 7.0 | 9.1 | 155 |
| Methylisobutylketone | 5.5 | 4.4 | 265 |
| Methyl-t-butyl ether | 5.8 | 5.1 | 321 |
| 2-MeTHF | 7.1 | 4.4 | 790 |
| Dichloromethane | 6.6 | 8.5 | 0 |
| Acetic Acid | 6.5 | 7.3 | 10 |
| n-Heptane | 6.0 | 3.7 | 276 |
| Toluene | 4.6 | 4.4 | 738 |
| Acetonitrile | 5.3 | 12.0 | 43 |
| Acetone | 4.6 | 12.0 | 108 |
| Dimethyl Carbonate | 5.4 | 4.1 | 115 |
| Nitromethane | 5.3 | 4.7 | 86 |

*TOF/sec for MA means turnover frequency of the catalyst for MA under those conditions

EXAMPLE 5: CATALYSTS FOR THE OXIDATION OF HFO TO MALEIC ACID IN TOLUENE

An autoclave (10 ml) was charged with HFO (10.6 mg), toluene (1 ml) and catalyst according to the Table 2. The reactor was sealed then flushed with nitrogen. The reactor was then charged to 10 bar of pressure with pure oxygen. The reactor was then heated to 111° C. and stirred for 14 hours. After cooling to ambient temperature, the pressure was released and the reactor flushed with nitrogen. The product solutions were then filtered to remove catalyst, then analyzed by HPLC, with the results compiled in Table 2.

TABLE 2

| Solvent | Catalyst (mg) | TOF/sec for MA |
|---|---|---|
| No Catalyst | — | 0 |
| Au/SiO2 | 94 | 3279 |
| Pd/C | 6.0 | 309 |
| Pt/C | 13 | 82 |
| Ru/C | 11 | 1464 |

* TOF/sec for MA means turnover frequency of the catalyst for MA under those conditions

The invention claimed is:

1. A process for preparing maleic acid or a derivative thereof, said process comprising a step b) of oxidizing 5-hydroxy-2(5H)-furanone and/or cis-β-formylacrylic acid to maleic acid or a derivative thereof by contacting said 5-hydroxy-2(5H)-furanone and/or cis-β-formylacrylic acid with molecular oxygen ($O_2$) in the presence of a catalyst.

2. The process according to claim 1, wherein said catalyst comprises a transition metal, metal salt, metal oxide or a phosphate.

3. The process according to claim 1, wherein said catalyst comprises a solid support selected from the group consisting of zirconia, silica, activated carbon, aluminum oxide, zinc oxide, and titanium dioxide.

4. The process according to claim 1, wherein said 5-hydroxy-2(5H)-furanone and/or cis-β-formylacrylic acid is/are liquid or dissolved in a solvent when contacted with said $O_2$.

5. The process according to claim 4, wherein said solvent comprises an organic solvent or an aqueous solvent.

6. The process according to claim 1, wherein said step b) is carried out under a pressure of at least 5 bar.

7. The process according to claim 1, wherein said step b) is carried out at a temperature in the range of 20 to 200° C.

8. The process according to claim 1, wherein said step b) is carried out in a continuous reactor.

9. The process according to claim 1, wherein said step b) is preceded by a step of providing 5-hydroxy-2(5H)-furanone and/or cis-β-formylacrylic acid in an isolated formulation.

10. The process according to claim 1, wherein the derivative of maleic acid is one or more selected from the group consisting of maleic anhydride, fumaric acid, succinic acid, succinonitrile, putrescine, malic acid, and salts, anhydrides, amide, imides and esters of any of these compounds.

11. The process according to claim 1, wherein said step b) of oxidizing said 5-hydroxy-2(5H)-furanone and/or cis-β-formylacrylic acid to maleic acid or a derivative thereof is preceded by a step a) of oxidizing a furanic compound according to formula I into said 5-hydroxy-2(5H)-furanone and/or cis-β-formylacrylic acid,

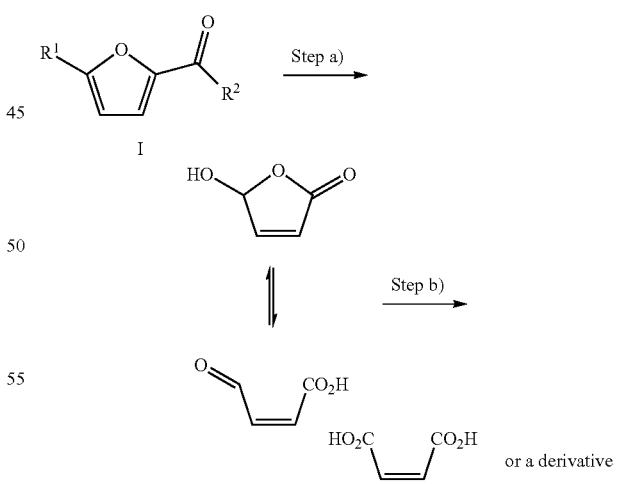

wherein $R^1$ is H, $CH_2OH$, $CO_2H$ or CHO and $R^2$ is H, OH, $C_1$-$C_6$ alkyl or $O(C_1$-$C_6$ alkyl), esters, ethers, amides, acid halides, anhydrides, carboximidates, nitriles, and salts of formula I.

12. The process according to claim 11, wherein said step a) comprises electrochemically oxidizing the furanic compound in an aqueous electrolyte solution.

13. The process according to claim 12, wherein said step a) and said step b) are carried out in said aqueous electrolyte solution.

14. The process according to claim 12, wherein said step a) is followed by an intermediate extraction step of extracting said 5-hydroxy-2(5H)-furanone and/or cis-β-formylacrylic acid with an organic solvent and wherein said step b) is carried out in said organic solvent.

15. The process according to claim 11, wherein said step a) comprises electrochemically oxidizing the furanic compound in an aqueous electrolyte solution comprising an acid.

16. The process according to claim 11, wherein said step a) comprises electrochemically oxidizing the furanic compound in an aqueous electrolyte solution comprising a mineral acid.

17. The process according to claim 11, wherein said step a) comprises electrochemically oxidizing the furanic compound in an aqueous electrolyte solution comprising a mineral acid selected from the group consisting of hydrochloric acid (HCl), nitric acid ($HNO_3$), phosphoric acid ($H_3PO_4$), sulfuric acid ($H_2SO_4$), boric acid ($H_3BO_3$), hydrofluoric acid (HF), hydrobromic acid (HBr), perchloric acid ($HClO_4$) and hydroiodic acid (HI).

18. The process according to claim 17, wherein the mineral acid is sulfuric acid.

19. The process according to claim 1, wherein said process further comprises converting said maleic acid into one or more of its derivatives selected from the groups consisting of maleic anhydride, fumaric acid, succinic acid, succinonitrile, putrescine, malic acid, and salts, anhydrides, amide, imides and esters of any of these compounds.

20. The process according to claim 1, wherein said catalyst comprises a transition metal, metal salt, metal oxide or a phosphate of which the metal is selected from the group consisting of cobalt, manganese, vanadium, molybdenum, copper, silver, gold, palladium, platinum and ruthenium.

21. The process according to claim 1, wherein said catalyst comprises a transition metal, metal salt, metal oxide or a phosphate of which the metal is gold.

* * * * *